(12) United States Patent
Woychik (10) Patent No.: US 6,221,647 B1
(45) Date of Patent: Apr. 24, 2001

(54) EFFICIENT CONSTRUCTION OF GENE TARGETING USING PHAGE-PLASMID RECOMBINATION

(75) Inventor: Richard Woychik, Beechwood, OH (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 09/262,445

(22) Filed: Mar. 4, 1999

Related U.S. Application Data (63) Continuation of application No. 08/962,313, filed on Oct. 31, 1997.

(51) Int. Cl.$^7$ .............................. C12N 15/72; C12N 15/73
(52) U.S. Cl. ...................................... 435/235.1; 435/320.1
(58) Field of Search .................................. 435/456, 463, 435/320.1, 235.1

(56) References Cited

U.S. PATENT DOCUMENTS

| | | | |
|---|---|---|---|
| 4,710,465 | * 12/1987 | Weissman et al. | 435/91.1 |
| 5,530,178 | 6/1996 | Mak | 800/2 |
| 5,625,122 | 4/1997 | Mak | 800/2 |

OTHER PUBLICATIONS

Ausubel et al., (Eds.), in *Current Protocols in Molecular Biology*, Chapter 5, "Construction of Recombinant DNA Libraries,"John Wiley & Sons, Inc. pp. 5.0. 1–5.112. (1987).
Barinaga, M., "Knockout Mice Offer First Animal Model for CF, "*Science*, 257:1046–1047 (1992)
Baudin, A. et al., "A simple and efficient method for direct gene deletion in *Saccharomyces cerevisiae*, "*Nucleic Acids Research*21 (14):3329–3330 (1993).
Bollag, R.J. et al., "Homologous Recombination in Mammalian Cells, "*Annu. Rev. Genet.*, 23:199–225 (1989).
Bradley, A. et al., "Embryo–Derived Stem Cells: A Tool for Elucidating the Developmental Genetics of the Mouse, "*Current Topics in Developmental Biology*, 20:357–371 (1986).
Chalfie, M. et al.,"Green Fluorescent Protein as a Marker for Gene Expression", *Science*, 263:802–805 (1994).
Chen, C. et al., "Abnormal Fear Response and Aggressive Behavior in Mutant Mice Deficient for α–Calcium–Calmodulin Kinase II,"*Science*, 266:291–294 (1994).
Christianson, T. W. et al., "Multifunctional yeast high–copy–number shuttle vectors", *Gene*, 110:119–122 (1992).
Dopf, J. et al., "Deletion mapping of the *Aequorea victoria*green fluorescent protein," *Gene*, 173:39–44 (1996).
Dorin, J.R. et al., "Successful targeting of the mouse cystic fibrosis transmembrane conductance regulator gene in embryonal stem cells," *Transgenic Research*, 1:101–105 (1992).

Fung–Leung, W–P et al.,"CD8 Is Needed for Development of Cytotoxic T Cells but Not Helper T Cells, " *Cell*, 65:443–449 (1991).
Geitz, R.D. et al., "High Efficiency Transformation with Lithium Acetate, " In *Molecular Genetics of Yeast, A Practical Approach*, J. R. Jonston, Ed., pp. 121–134 (1995).
Gu, H. et al., "Deletion of a DNA Polymerase βGene Segment in T Cells Using Cell Type–Specific Gene Targeting," *Science*, 265:103–106(1994).
Guthrie, C. et al., Eds. in *Methods in Enzymology: Guide to Yeast Genetics and Molecular Biology*, vol. 194, Academic Press, pp. 182–187, 239–251, 319–329, 373–388, and 389–398 (1991).
Hamer, R.E. et al., "Production of transgenic rabbits, sheep and pigs by microinjection, " *Nature*, 315:680–683 (1985).
Hanks, M. et al., "Rescue of the *En–1*Mutant Phenotype by Replacement of *En–1*with *En2*, " *Science*269:679–682 (1995).
Hoffman, C.S. et al., "A ten–minute DNA preparation from yeast efficiently releases autonomous plasmids for transformation of *Escherichia coli*, " *Gene*, 57:267–272 (1987).
Hogan et al. in *Manipulating the Mouse Embryo: A Laboratory Manual*, Cold Spring Harbor Laboratory Press, Cold Spring Harbor New York, pp. 91–149, 153–197, and 247–267 (1986).
Joyner, A. L. et al.,"Production of a mutation in mouse *En–2*gene by homologous recombination in embryonic stem cells, " *Nature*, 338:153–156 (1989).
Joyner, A.L., (ed.) in *Gene Targeting: A Practical Approach*, IRL Press, Oxford University Press, New York, pp. 107–144 and 147–178 (1993).
Knudsen, C.M. et al., "Bax–Deficient Mice with Lymphoid Hyperplasia and Male Germ Cell Death, "*Science*, 270:96–99 (1995).
Koller, B.H. et al., "Toward an animal mode of cystic fibrosis: Targeted interruption of exon 10 of the cystic fibrosis transmembrane regulator gene in embryonic stem cells, " *Proc. Natl. Acad. Sci., USA*, 88:10730–10734 (1991).
Lorenz, M.C. et al., "Gene disruption with PCR products in *Saccharomyces cerevisiae*, " *Gene*, 158:113–117 (1995).
Luo, Y. et al., "A Novel Method for Monitoring *Mycobacterium bovis*BCG Trafficking with Recombinant BCG Expressing Green Fluorescent Protein, "*Clinical Diagnostic Laboratory Immunology*, 3(6):761–768 (1996).
Lutz, C.T. et al., "Syrinx 2A: An improved λphage vector designed for screening DNA libraries by recombination in vivo, " *Proc. Natl. Acad. Sci. USA*, 84:4379–4383 (1987).
Manivasakam, P. et al., "Micro–homology mediated PCR targeting in *Saccharomyces cerevisiae*, " *Nucleic Acids Research,*23(14):2799–2800 (1995).

(List continued on next page.)

Primary Examiner—James Ketter
(74) Attorney, Agent, or Firm—Marshall, O'Toole, Gerstein, Murray & Borun (57) ABSTRACT

A method for producing gene targeting constructs in bacterial by way of homologous recombination between bacterial phage and plasmids.

13 Claims, 6 Drawing Sheets

OTHER PUBLICATIONS

Marx, J., "Knocking Genes In Instead of Out," *Science*, 269:636 (1995).

Michaud, E.J. et al., "The embryonic lethality of homozygous lethal yellow mice ($A^y/A^y$) is associated with the disruption of a novel RNA–binding protein, " *Genes & Development*, ∂:1203–1213 (1993).

Miki, Y. et al., "A Strong Candidate for the Breast and Ovarian Cancer Susceptibility Gene *BRCA1*, " *Science*, 266:66–71 (1994).

Mansour, S.L. et al., "Disruption of the proto–oncogene *int*–2in mouse embryo–derived stem cells: a general strategy for targeting mutations to non–selectable genes," *Nature*, 336:348–352 (1988).

Moyer, J.H. et al., "Candidate Gene Associated with a Mutation Causing Recessive Polycystic Kidney Disease in Mice," *Science*, 264:1329–1333 (1994).

Oldenbburg, K.R. et al., "Recombination–mediated PCR–directed plasmid construction in vivo in yeast, " *Nuclei Acids Research*, 25(2);451–452 (1997).

Orr–Weaver, T. L. et al., "Fungal Recombination," *Microbiological Reviews*, 49(1):33–58 (1985).

Robertson, E.J. (ed.) in *Teratocarcinomas and embryonic stem cells, a practical approach*, IRL Press, Washington D.C., pp. 113–181 (1987).

Sambrook et al., *Molecular Cloning: A Laboratory Maual*, section pp. 1.19, 1.74–1.75,2.6,8.2–8.86, and 9.2–9.58 Cold Spring Harbor Laboratories (1989).

Seed, B., "Purification of genomic sequences from bacteriophage libraries by recombination and selection in vivo, " *Nucleic Acids Research*, 11(8):2427–2445 (1983).

Sikorski, R.S. et al., "A System of Shuttle Vectors and Yeast Host Strains Designed for Efficient Manipulation of DNA in *Saccharomyces cerevisiae*, " *Genetics*, 122;19–27 (1989).

Silva, A.J. et al., "Deficient Hippocampal Long–Term Potentiation in α–Calcium–Calmodulin Kinase II Mutant Mice, "*Science*, 257:201–206 (1992).

Snouwaert, J.N. et al., "An Animal Model for Cystic Fibrosis Made by Gene Targeting," *Science*, 257: 1083–1088 (1992).

Soriano et al., "Targeted Disruption of the *c–src*Proto–Oncogene Leads to Osteopetrosis in Mice," *Cell*, 64:693–702 (1991).

Storck, T. et al., "Rapid construction in yeast of complex targeting vectors for gene manipulation in the mouse," *Nuclei Acids Research*, 24(22):4594–4596 (1996).

Tavtigian, S.V. et al., "The complete *BRCA2*gene and mutations in chromosome 13q–linked kindreds, "*Nature Genetics*, 12:333–337 (1996).

Thomas K.R.et al., "Site–Directed Mutagenesis by Gene Targeting in Mouse Embryo–Derived Stem Cells, " *Cell*, 51:503–512 (1987).

Travis, J."Scoring a Technical Knockout in Mice," *Science*, 256:1392–1394 (1992).

Veis, D.J. et al., "Bcl–2–Deficient Mice Demonstrate Fulminant Lymphoid Apoptosis, Polycystic Kidneys, and Hypopigmented Hair, " *Cell*, 75:229–240 (1993).

Wang, N. et al., "Impaired Energy Homeostasis in C/EBPα Knockout Mice, " *Science*, 269 1108–1112 (1995).

Zhang, Y. et al, "Positional cloning of the mouse *obese*gene and its human homologue, " *Nature*, 372:425–432 (1994).

Tsuzuki et al., "Embryonic stem cell gene targeting using bacteriophage lambda vectors generated by phage–plasmid recombination", *Nucleic Acids Research*, vol. 26(4):988–993 (Feb. 15, 1998).

International Search Report dated Oct. 2, 1998, International Application No. PCT/US98/1151.

* cited by examiner

EFFICIENT CONSTRUCTION OF GENE TARGETING USING PHAGE-PLASMID RECOMBINATION

This is a continuation of U.S. application Ser. No. 08/962,313, filed Oct. 31, 1997.

BACKGROUND OF THE INVENTION

One of the most useful approaches for studying the functions of specific genes (including their health related functions) is to examine the effects of mutations within those genes (i.e., the phenotype of the mutation). This approach involves correlating mutations within specific genes with the phenotypes or disease conditions that result from those mutations. This has been particularly fruitful in recent years with the identification of genes for such diseases as cystic fibrosis (Snouwaert et al., *Science*, 257:1083 (1992)), obesity (Zhang et al, *Nature*, 372: 425 (1994)), polycystic kidney disease (Moyer et al., *Science*, 264:1329 (1994)), breast cancer [Miki et al., *Science*, 266:66–71 (1994); Tavtigian et al., *Nat. Genet.*, 12:333–337 (1996)], and other diseases. In these cases, the function of the implicated genes was not apparent solely from their DNA sequence but rather was defamed by a disease condition associated with mutations in the genes.

A particularly productive approach to understanding the function of a particular gene in animals involves the disruption of the gene's function which is colloquially referred to as a "targeted mutagenesis". One common form of targeted mutagenesis involves generating "gene knockouts". Typically, a gene knockout involves disrupting a gene in the germline of an animal at an early embryonic stage. (See, Thomas et al., *Cell*, 51:503 (1987).) Once established in the germline, it is possible to determine the effect of the mutation on the animal in both the heterozygous and homozygous states by appropriate breeding of mice having the germline mutation.

Among the many examples of the use of knockout technology utilized to investigate gene function are U.S. Pat. Nos. 5,625,122 and 5,530,178 to Mak, T. which describe the production of mice having a disrupted gene encoding lymphocyte-specific tyrosine kinase $p56^{lck}$ and Lyt-2, respectively. Silva et al., *Science*, 257:201 (1992) produced mice having a disrupted α-Calcium Calmodulin kinase II gene (αCaMKII gene) which resulted in animals having an abnormal fear response and aggressive behavior. (See, also, Chen et al., *Science*, 266:291 [1994]). Wang et al., *Science*, 269:1108 (1995) demonstrated that the disruption in mice of the C/EPBα gene which encodes a basic leucine zipper transcription factor results in impaired energy homeostasis in the mutant animals. Knudsen et al., *Science*, 270:960 (1995) demonstrated that disruption of the BAX gene in mice results in lymphoid hyperplasia and male germ cell death.

The most common approach to producing knockout animals involves the disruption of a target gene by inserting into the target gene (usually in embryonic stem cells), via homologous recombination, a DNA construct encoding a selectable marker gene flanked by DNA sequences homologous to part of the target gene. When properly designed, the DNA construct effectively integrates into and disrupts the targeted gene thereby preventing expression of an active gene product encoded by that gene.

Homologous recombination involves recombination between two genetic elements (either extrachromosomally, intrachromosomally, or between an extrachromosomal element and a chromosomal locus) via homologous DNA sequences, which results in the physical exchange of DNA between the genetic element. Homologous recombination is not limited to mammalian cells but also occurs in bacterial cells, yeast cells, in the slime mold *Dictyostelium discoideum* and in other organisms. For a review of homologous recombination in mammalian cells, see Bollag et al., *Ann. Rev. Genet.*, 23:199–225 (1989) (incorporated herein by reference). For a review of homologous recombination in fungal cells, see Orr-Weaver et al., Microbiol. Reviews, 49:33–58 (1985) incorporated herein by reference.

As is illustrated by the foregoing, gene knockout technology has often been used in mice and has allowed the identification of the function of numerous genes and, in some cases, ascertainment of their roles in disease. Much may be learned about the function of human genes from studies of mouse genetics because the vast majority of genes in humans have homologous counterparts in the mouse. Because of this high level of homology between the species, it is now possible to defame the function of individual human genes and to elucidate their roles in health and disease by making targeted germline mutations in selected genes in the mouse. The phenotype of the resulting mutant mice can be used to help define the phenotype in humans.

With the increasing awareness that mouse mutations can provide such useful insights about the function of genes from humans, a great deal of interest is developing to systematically generate mutations within genes in mice that correspond to those genes which are being isolated and characterized as part of various genome initiatives such as the Human Genome Project. The problem with utilizing these procedures for large-scale mutagenesis experiments is that the technologies for generating transgenic animals and targeted mutations are currently very tedious, expensive, and labor intensive.

One of the biggest problems with the efficient generation of targeted mutations is the generation of the targeting construct. Targeting constructs are typically prepared by isolating genomic clones containing the region of interest, developing restriction maps, frequently engineering restriction sites into the clones, and manually cutting and pasting fragments to engineer the construct. See, e.g., Mak, T. U.S. Pat. Nos. 5,625,122 and 5,530,178; Joyner et at., *Nature*, 338:153–156 (1989); Thomas et al., supra; Silva et al., supra, Chen et al., supra; Wang et al., supra; and Knudsen et al., supra. This process can take a single highly skilled individual at least several weeks, often several months, to complete. Thus, in order to more rapidly and efficiently elucidate the functions of a variety of genes and to understand their role in health and disease, there exists a need to develop more efficient methods for the production of targeting constructs which do not require detailed restriction mapping and certain other complex molecular engineering steps.

SUMMARY OF THE INVENTION

The invention is directed to methods for producing gene targeting constructs by way of homologous recombination between bacteriophage and plasmids. More particularly, the invention is directed to methods for producing gene targeting constructs in bacteria by way of single homologous recombination events. The method comprises the steps of preparing a probe plasmid comprising a suppressor tRNA gene, preferably a bacterial replication origin and a probe DNA, the probe DNA comprising at least a portion of a gene (e.g., exon) to be targeted. The probe plasmid is introduced into a population of homologous recombination proficient, suppressor-free bacterial host cells.

The method further comprises preparing a target phage comprising at least one suppressible mutation in a gene necessary for phage growth and a target DNA, the target DNA comprising a portion of a genomic region to be targeted and which is homologous to all or part of the probe DNA of the probe plasmid. The population of bacterial cells containing the probe plasmid is then infected with the target phage phage and probe plasmid are allowed to recombine via their homologous DNA. Recombinant phage may then be isolated by virtue of their ability to grow on a suppressor-free host cell by virtue of its incorporation of the suppressor tRNA gene from the probe plasmid into the target phage.

Preferably, the probe DNA of the probe plasmids comprises at least about 20 nucleotides to about 40 nucleotides of probe DNA. A preferred suppressor tRNA gene for the practice of the present invention is SupF, an amber suppressor. The probe plasmid of the present invention may further comprise a marker cassette, the marker cassette comprising the suppressor tRNA gene and a mammalian cell selectable marker with the marker cassette being flanked on at least one side by probe DNA. Preferably, the marker cassette is flanked on both sides by at least about 20 nucleotides to 40 nucleotides or more of probe DNA. A preferred mammalian cell selectable marker for the practice of the present invention is the neo gene. However, other reporter genes such as those that confer antibiotic resistance to cells expressing the gene or marker genes which allow chemical or physical detection are also contemplated as being within the scope of the present invention. The mammalian cell selectable marker is preferably, operatively linked to a promoter capable of allowing expression of the selectable marker gene in embryonic stem cells. A preferred promoter, according to the present invention, is the phophoglycerate kinase (PGK) promoter although other promoters which may function in embryonic stem cells are well known in the art and fall within the scope of the present invention. Preferred bacteria phage for practice of the present invention is a lambda phage, although other bacteriophage may be used in the practice of the invention.

The invention is also directed to methods for producing targeting constructs by way of double recombination. The method comprises the steps of preparing a circular probe plasmid/specific engineered fragment (SEF) comprising a marker cassette, the marker cassette comprising a suppressor tRNA gene and a mammalian selectable marker, the marker cassette being flanked on each side by probe DNA homologous to a gene to be targeted, and linker DNA, the linker DNA serving to link the probe DNA flanking the marker cassette so as to form a circular plasmid. The circular probe plasmid is then introduced into a population of recombination proficient suppressor-free bacterial host cells. The method further comprises preparing a target phage. The target phage comprises at least one suppressible (e.g., amber) mutation in a gene necessary for phage growth and a target DNA comprising a portion of a genomic region to be targeted. The target DNA comprises DNA sequences homologous to all or part of probe DNA on the circular probe plasmid. The target phage is then used to infect the population of bacterial cells containing the probe plasmid/SEF and the phage and plasmid are allowed to recombine via their homologous DNA. The phage produced by homologus recombination in the infected cells are then isolated, as described above, for use as targeting constructs.

Preferably, the probe DNA of the circular probe plasmid each comprises more than about 40 bp of probe DNA. In a preferred embodiment of the present invention, the suppressor tRNA gene is SupF. A preferred mammalian cell selectable marker for the practices of the invention is a neo gene, although other markers which confer, for example, antibiotic resistance or which are chemically or physically detectable are also contemplated as falling within the scope of the present invention. The mammalian cell selectable markers are preferably operatively linked to a promoter capable of driving expression of the marker gene in an embryonic stem cell. A preferred promoter for the practice of the invention is the phosphoglycerate kinase promoter (PGK), although other promoters which are capable of driving expression of a gene in embryonic stem cells are also within the scope of the invention. A preferred phage for the practice of the present invention is a lambda phage.

The invention is also directed to targeting constructs produced by or obtainable by the methods of the present invention.

Another aspect of the present invention is directed to a method for producing or obtaining targeting constructs comprising culturing under suitable nutrient and environmental conditions a population of homologous recombination proficient bacterial cells comprising a target phage of the invention and a probe plasmid or probe plasmid/SEF of the present invention and isolating the phage resulting from homologous recombination between the target phage and the respective plasmids.

DETAILED DESCRIPTION

In one of its aspects, the present invention is directed to methods for producing targeting constructs for the purpose of introducing into the genome of an animal, a disruption at a particular genetic locus (i.e., a targeted mutation). The targeting constructs of the present invention may also be used to introduce into a genomic locus another functional gene ("knock in") or to otherwise alter the function or expression of a gene, for example, by knocking in a foreign promoter so as to place it in operative linkage with a gene in a chromosomal locus. The targeting construct is inserted into the appropriate genome location by taking advantage of the cell's ability to mediate homologous recombination between homologous sequences in the targeting construct and the sequences in the genomic region or gene of interest.

Unlike traditional methods for constructing targeting constructs, the practice of the present invention does not require detailed restriction maps or extensive DNA sequence information in order to prepare targeting constructs. Because such detailed information is not required to prepare targeting constructs according to the present invention, vectors may be produced more quickly and effectively than previously employed methods.

More specifically, targeted mutagenesis of a gene refers to an alteration (e.g., partial or complete inactivation) of normal production or structure of the polypeptide encoded by the targeted gene of a single cell, selected cells or all of the cells of an animal (or in culture) by introducing an appropriate targeting construct into a site in the gene to be disrupted.

Targeted mutagenesis may also refer to "knocking in" a gene which means replacing one gene with all or part of another gene for the purpose of determining, for example, whether two genes are functionally equivalent (see, e.g., Hanks et al., *Science*, 269:679 (1995), incorporated herein by reference), although other applications are possible. For example, transcriptional regulatory sequences (elements) such as promoters may be knocked in to a region of a genome so as to become operatively linked to a structural gene thereby controlling expression of structural gene. In some cases the transcriptional regulatory sequence may be knocked into regions flanking the structural gene and yet still be positioned in operation linkage with the gene.

In most cases, targeting constructs are constructed so as to include at least a portion of a gene to be disrupted. Typically, the portion of the gene included in the targeting construct is interrupted by insertion of a marker sequence (usually a selectable marker) that disrupts the reading frame of the interrupted gene so as to preclude expression of an active gene product. This most often causes a knock out or inactivation of a gene. An exemplary selectable marker is the neo' gene under the control of a promoter that functions in the embryonic cells into which the marker is introduced. For example, the phosphoglycerate kinase promoter (PGK) may be used to control expression of the neo gene thereby rendering the cells expressing the neo' gene resistant to G418, although other promoters capable of driving expression of the selectable marker in ES cells may also be used.

Prior to the present invention, the preparation of targeting constructs typically involved detailed restriction mapping in order to identify convenient restriction sites in the gene fragment to be used to "cut and paste" DNA fragments to ultimately generate a targeting vector. However, mapping frequently reveals that convenient restriction sites are not available and therefore, they must be engineered into various components of the targeting constructs. According to the present invention, detailed mapping and sequence information are not required in order to prepare targeting constructs which results in a significant saving of time and effort in preparing targeting constructs.

When such targeting constructs are introduced into embryonic stem cells, they can recombine with the target gene in the cell via the homologous sequences in both the construct and in the gene genomic region to be disrupted. As discussed above, the result of the homologous recombination event is often the insertion of a marker sequence into the targeted gene, thereby disrupting the gene. Similarly, targeting constructs designed for knocking in genes can recombine at the homologous genomic site by homologous recombination and will result in the introduction of all or a portion of a gene into that locus. Techniques for knocking in genes are described in detail in Hanks et al., Science, 269:679 (1995) which is incorporated herein by reference.

In order to introduce the targeting construct into the germline of an animal, the targeting construct is first introduced into an undifferentiated totipotent cell termed an embryonic stem (ES) cell wherein the construct can recombine with the selected genomic region via their homologous sequences. ES cells are derived from an embryo or blastocyst of the same species as the developing embryo into which they are to be introduced. ES cells are typically selected for their ability to integrate into the inner cell mass and contribute to the germ line of an individual when introduced into the mammal in an embryo at the blastocyst stage of development. Thus, any ES cell line having this capability is suitable for use in the practice of the present invention.

The cells are cultured and prepared for introduction of the targeting construct using methods well known to the skilled artisan. (See, e.g., Robertson, E. J. ed. "Teratocarcinomas and Embryonic Stem Cells, a Practical Approach", IRL Press, Washington D.C. [1987]; Bradley et al., *Current Topics in Devel. Biol.* 20:357–371 [1986]; by Hogan er al. in "Manipulating the Mouse Embryo": A Laboratory Manual, Cold Spring Harbor Laboratory Press, Cold Spring Harbor New York [1986]; Thomas et al., *Cell*, 51:503 [1987]; Koller et al., *Proc. Natl. Acad. Sci. USA*, 88:10730 [1991]; Dorin et al., *Transgenic Res.*, 1:101 [1992]; and Veis et al., *Cell*, 75:229 [1993] all of which are incorporated herein by reference). The targeting construct may be introduced into ES cells by any one of several methods known in the art including electroporation, calcium phosphate co-precipitation, retroviral infection, microinjection, lipofection and other methods. Insertion of the targeting construct into the targeted gene is typically detected by selecting cells for expression of the marker gene contained in the targeting construct which, as described above, is typically under the control of a promoter which is functional in the target cell type (i.e., promoters which function in embryonic stem cells). ES cells expressing the marker sequence are then isolated and expanded.

The ES cells having the disruption are then introduced into an early-stage mouse embryo (e.g., blastocyst) (see, e.g., Robertson, supra, Bradley, supra, and Monsour et al., *Nature*, 336:348 (1988)) incorporated herein by reference. Blastocysts and other early stage embryos used for this purpose are obtained by flushing the uterus of pregnant animals for example, by the methods described in Robertson et al., supra and Bradley et al., supra. The suitable stage of development for the blastocyst is species dependent, however, for mice it is about 3.5 days post-fertilization.

While any embryo of the right age/stage of development is suitable for implantation of the modified ES cell, preferred most embryos are male and have genes coding for a coat color or other phenotypic marker that is different from the coat color or other phenotypic marker encoded by the ES cell genes. In this way, the offspring can be screened easily for the presence of the targeted mutation by looking for mosaic coat color (e.g. agouti) or the other phenotypic markers (indicating that the ES cell was incorporated into the developing embryo). Thus, for example, if the ES cell line carries the genes for white fur, the host embryos selected will preferably carry genes for black or agouti fur.

An alternate method of preparing an embryo containing ES cells that possess the targeting construct is to generate "aggregation chimeras". A morula of the proper developmental stage (about 2½ days post-fertilization for mice) is isolated. The zona pellucida can be removed by treating the morula with a solution of mild acid for about 30 seconds, thereby exposing the "clump" of cells that comprise the morula. Certain types of ES cells such as the R1 cell line for mice can then be co-cultured with the morula cells, forming an aggregation chimera embryo of morula and ES cells, (Joyner, A. L., "Gene Targeting", *The Practical Approach Series*, JRL Press Oxford University Press, New York, 1993, incorporated herein by reference).

A refinement of the aggregation chimera embryo method can be used to generate an embryo comprised of essentially only those ES cells containing the knockout construct. In this technique, a very early stage zygote (e.g., a two-cell stage zygote for mice) is given a mild electric shock. This shock serves to fuse the nuclei of the cells in the zygote thereby generating a single nucleus that has two-fold (or more) the DNA of a naturally occurring zygote of the same developmental stage. These zygotic cells are excluded from the developing embryo proper, and contribute only to forming accessory embryonic structures such as the extra-embryonic membrane. Therefore, when ES cells are co-cultured with the zygotic cells, the developing embryo is comprised exclusively of ES cells, (see Joyner, A.L., supra).

After the ES cells have been incorporated into the aggregation chimera or into the blastocyst, the embryos may be implanted into the uterus of a pseudopregnant foster mother. While any foster mother may be used, preferred foster mothers are typically selected for their ability to breed and reproduce well, and for their ability to care for their young. Such foster mothers are typically prepared by mating with vasectomized males of the same species. The pseudopregnant stage of the foster mother is important for successful implantation, and it is species dependent. For mice, this stage is about 2–3 days of pseudopregnancy.

Offspring that are born to the foster mother may be screened initially for mosaic coat color or another phenotypic marker (where the phenotype selection strategy has been employed). In addition, or as an alternative, chromosomal DNA obtained from tail tissue of the offspring may be screened for the presence of the targeted mutation using Southern blots and/or PCR. The offspring that are positive for homologous recombination at the targeted locus will typically be a mosaic of wild-type cells derived from the host embryo and heterozygous cells derived from injected ES cells (i.e., chimeric offspring). Chimeric offspring are crossed with wild-type partners to generate offspring that are heterozygous for the targeted mutations, i.e., all of their cells are heterozygous for the mutation.

Methods for producing transgenic mammals, including rabbits, pigs, and rats, using micro-injection are described in Hamer et al., *Nature* 315:690–683 (1985).

If animals homozygous for the targeted mutation are desired, they can be prepared by crossing animals heterozygous for the targeted mutation. Mammals homozygous for the disruption may be identified by Southern blotting of equivalent amounts of genomic DNA from mammals that are the product of this cross, as well as mammals of the same species that are known heterozygotes, and wild-type mammals. Alternatively, specific restriction fragment length polymorphisms can be detected which co-segregate with the mutant locus. Probes to screen the Southern blots for the presence of the targeting construct in the genomic DNA can be designed as described below.

Other means of identifying and characterizing the offspring having a disrupted gene are also available. For example, Northern blots can be used to probe mRNA obtained from various tissues of the offspring for the presence or absence of transcripts. Differences in the length of the transcripts encoded by the targeted gene can also be detected. In addition, Western blots can be used to assess the level of expression of the targeted gene by probing the Western blot with an antibody against the protein encoded by the targeted gene. Protein for the Western blot may be isolated from tissues where this gene is normally expressed. Finally, in situ analysis (such as fixing the cells and labeling with antibody or nucleic acid probe) and/or FACS (fluorescence activated cell sorting) analysis of various cells from the offspring can be conducted using suitable antibodies to look for the presence or absence of the gene product.

While the foregoing discussion describes the use of targeting constructs to introduce DNA into a genomic locus via homologous recombination, the process of homologous recombination may also, according to the present invention, be used to prepare the targeting constructs themselves.

The methods of the present invention exploit certain aspects of the πVX screening procedure described by Seed (*Nucleic Acid Res.* 11:2427–2445, 1980) and allows the rapid generation of target vectors for the introduction of mutations into mice, without the necessity of a detailed restriction map and with limited DNA sequence information. The methods of the present invention take advantage of the ability of DNA sequences in a plasmid to recombine with homologous DNA in a bacteriophage ("phage") with the resulting insertion of at least a portion of plasmid-born DNA into the phage.

By way of overview, the invention is directed to a method for preparing targeting constructs by preparing a "probe" plasmid construct comprising DNA homologous to a gene to be targeted (probe DNA), a suppressor t-RNA gene and preferably a gene encoding a mammalian selectable marker. A target phage having DNA comprising at least a portion of a gene to be disrupted and which has homology to the DNA in the "probe" plasmid and one or more suppressible mutations in genes important for growth of the phage is also prepared. The probe plasmid is then introduced into a population of recombination competent bacterial cells. The population of cells containing the probe plasmid is then infected with the target phage. The target phage and the probe plasmid can then recombine via their aforementioned homologous DNAs which results in the insertion of probe plasmid sequences into the homologous region of the phage insert via their homologous sequences. The recombined phage can then be isolated, amplified and used as a targeting construct for mammalian cells.

In another aspect of the invention, a probe plasmid is prepared in which "probe" DNA comprising a portion of a cDNA or genomic DNA to be targeted are inserted into a small plasmid containing a suppressor t-RNA gene. Exemplary plasmids include πVX (Seed, supra), πAN13 (Sambrook el al., Molecular Cloning: A Laboratory Manual, section p. 1.19, Cold Spring Harbor Laboratories (1989)), and πAN7 (Lutz et al., *Proc. Natl. Acad. Sci. USA*, 84:4379 (1987) and Ausubel et al., p. 5.0.1–5.11.2 (incorporated herein by reference)). Methods for producing cDNA libraries from which to obtain the relevant cDNA are well known in the art and are described in Sambrook et al., p. 8.2–8.93 (incorporated herein by reference). The probe plasmid may also comprise a marker for selection in mammalian cells (e.g., embryonic stem cells). The mammalian marker may allow biochemical selection, e.g., by conferring resistance to an antibiotic, e.g., or physical selection, e.g., expression of a fluorescent protein luciferase, or other markers whose expression may be detected by physical means. Preferably, the selectable marker is flanked on each end by probe DNA. Such flanking probe DNA is preferably at least about 20 to about 40 bp in length. The probe plasmid is then introduced into recombination-proficient bacterial cells (suppressor-less) by, for example, electroporation. Other methods for introducing plasmids into cells are described in Sambrook et al., supra and are well known in the art. Probe plasmids for use in preparing targeting constructs for knocking in promoter sequences, for example, comprise a marker cassette in which the selectable marker and the suppressor t-RNA gene are in 5' juxtaposition to the DNA to be knocked in. Alternatively, probe plasmids called specific engineered fragments (SEF) may be constructed which comprise the selectable markers and 40 or more base pairs of probe DNA flanking each side of a spacer or linker DNA. Such SEFs are useful for generating target constructs by double homologous recombination.

The population of bacterial cells containing the probe plasmid is then infected with target phage containing the genomic site to be targeted. An amber mutation in a gene or genes of the phage that regulate lytic growth is important. The target phage may be obtained from a genomic library prepared by methods well known in the art and described in detail in Sambrook et al., p. 9.2–9.58 or Ausubel et al., p. 5.0.1–5.11.2, both of which are incorporated herein by reference. Preferably, the vector phage also has an amber suppressible mutation in a gene which, when the mutation suppressed, is readily detectable, e.g., genes for lytic growth or an lacZ encoding β-galactosidase.

Cells containing the probe plasmid are then infected with a target phage such as those described above, after which the probe plasmid recombines with the target phage by homologous recombination between their homologous sequences. Only those phage that incorporate the gene via homologous recombination with the probe plasmid will be able to grow on suppressor-free host cells and can thus be readily isolated. Insertion of plasmid sequences including the selectable marker into phage interrupts the gene sequence carried by the target phage.

DNA isolated from these newly generated phage can then be used as targeting constructs to introduce targeted mutations, for example, in ES cells using methods described above. The examples set out below use the mouse Tg737 gene as a model to test how efficiently the targeting constructs could be generated by homologous recombination in bacteria.

Example 1 describes the production of targeting constructs by single homologous recombination.

Example 2 describes the production of targeting vectors by double homologous recombination using probe plasmids referred to as specific engineered fragments.

The approach is illustrated with reference to particular plasmids and particular phage. However, other plasmids having similar characteristics including suppressor genes and the ability to carry fragments of genomic or cDNA and other appropriate selectable markers may be used. Similarly, different phage may also be used so long as it contains appropriate suppressible mutations which may be complemented by the t-RNA suppressor genes provided by the plasmid.

EXAMPLE 1

Generation of Targeting Vectors by Single Homologous Recombination in Bacterial Host Cells A model system was used to demonstrate that targeting vector can be prepared by taking advantage of the fact that homologous recombination can occur between target phage and probe plasmids in bacterial cells. As a model gene, the mouse Tg737 was utilized (Moyer et al., *Science*, 264:1329 (1994) incorporated herein by reference).

Figure 1:
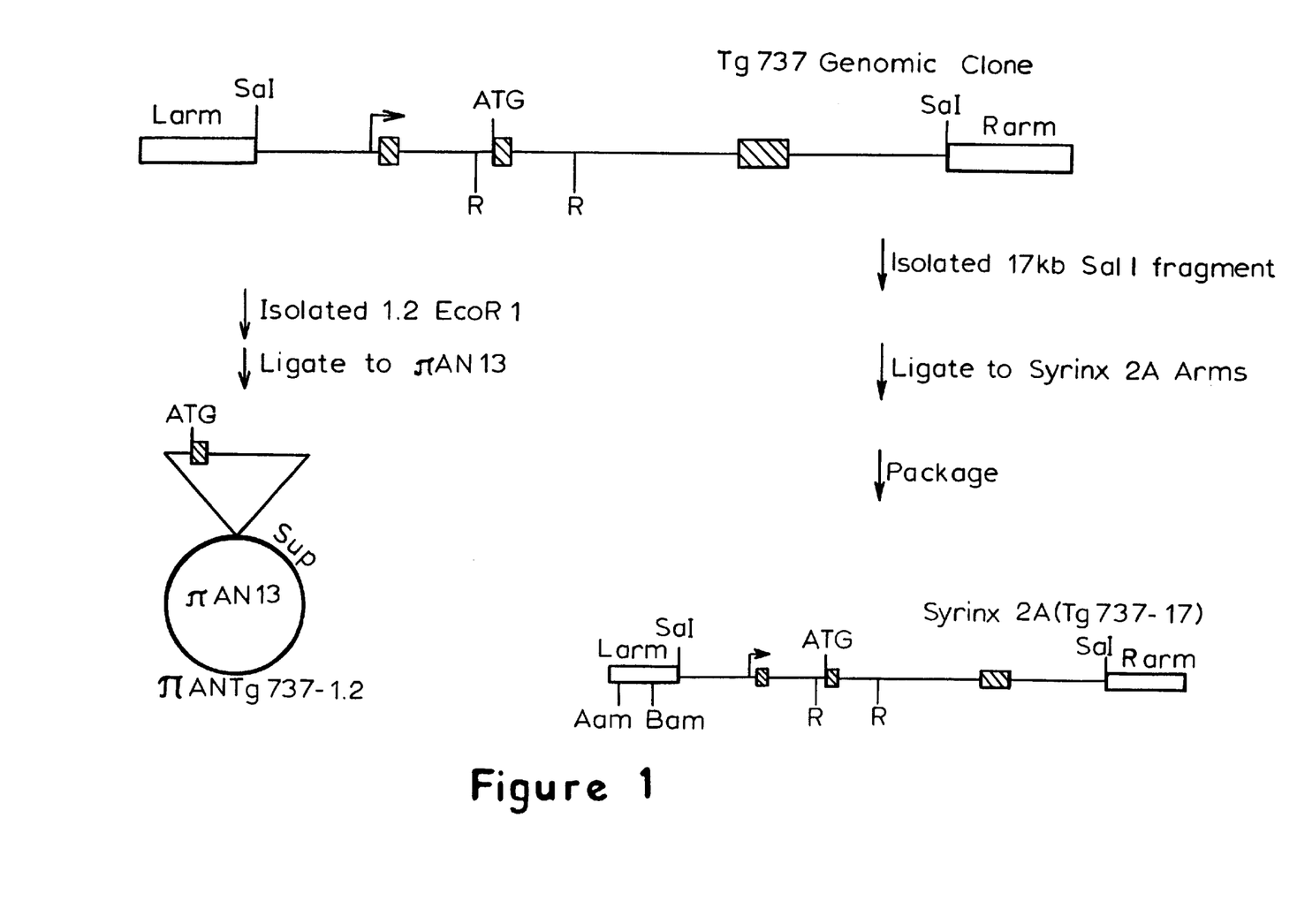
FIG. 1 depicts schematically the probe plasmid πANTg737-1.2 and Syrinx 2A (Tg737-17).

To generate a target phage comprising a lambda phage bearing amber mutations, a 17 kb SalI insert of a wild-type genomic clone containing a portion of the mouse Tg737 gene (including exon II of the genes), (target gene) was subcloned into Syrinx 2A phage arms (Lutz et al., *Proc. Natl. Acad. Sci. USA*, 84:4379 [1987] incorporated herein by reference) and the phage was packaged using methods well known in the art (see FIG. 1). Although a 17 kb portion of the Tg737 gene was used in this example, the size of the gene used in the target phage may vary. Preferred sizes are from about 15 kb–20 kb. Further, the insert need not be a portion of a genomic DNA, but may also be a portion of a cDNA. Syrinx 2A phage, a lambda phage vector, carries multiple cloning sites and a rap gene, which is required for efficient phage-plasmid recombination. The Syrinx 2A phage has amber mutations in the lambda A, B, and S genes which are essential for lytic growth and therefore, the frequency of spontaneous reversion is very low. The resulting phage carrying the target Tg737 DNA is called Syrinx 2A (Tg737-17).

In order to prepare a probe plasmid, a 1.2 kb EcoRI genomic fragment of the Tg737 gene including the ATG containing exon II of Tg737 (probe DNA) was isolated from the cloned genomic sequences and inserted in the πAN13 plasmid (see Sambrook et al., supra and Lutz et al., supra) to generate the probe plasmid πANTg737-1.2 (see FIG. 1); stretches of sequence as short as 20–40 bp can also be used for these experiments. Probe DNA may also be derived from a cDNA as well as a genomic DNA. The πAN13 plasmid is a high copy number miniplasmid which is designed for efficient recombination screening and includes a supF gene capable of producing a suppressor t-RNA capable of suppressing the amber mutation found in the Syrinx 2A (Tg737-1.2).

Plasmid πANTg737 plasmid was then introduced into *E. coli* MC1061 (sup0) by electroporation (see Sambrook et al., p. 1.74–1.75). The resulting population of *E. coli* containing πANTg737-1.2 was then infected with Syrinx 2A (Tg737-17) using routine methods (see Sambrook et al., p. 2.6 et seq.) and homologous recombination was allowed to occur between Syrinx 2A (Tg737-17) and πANTg737-1.2

Figure 2:
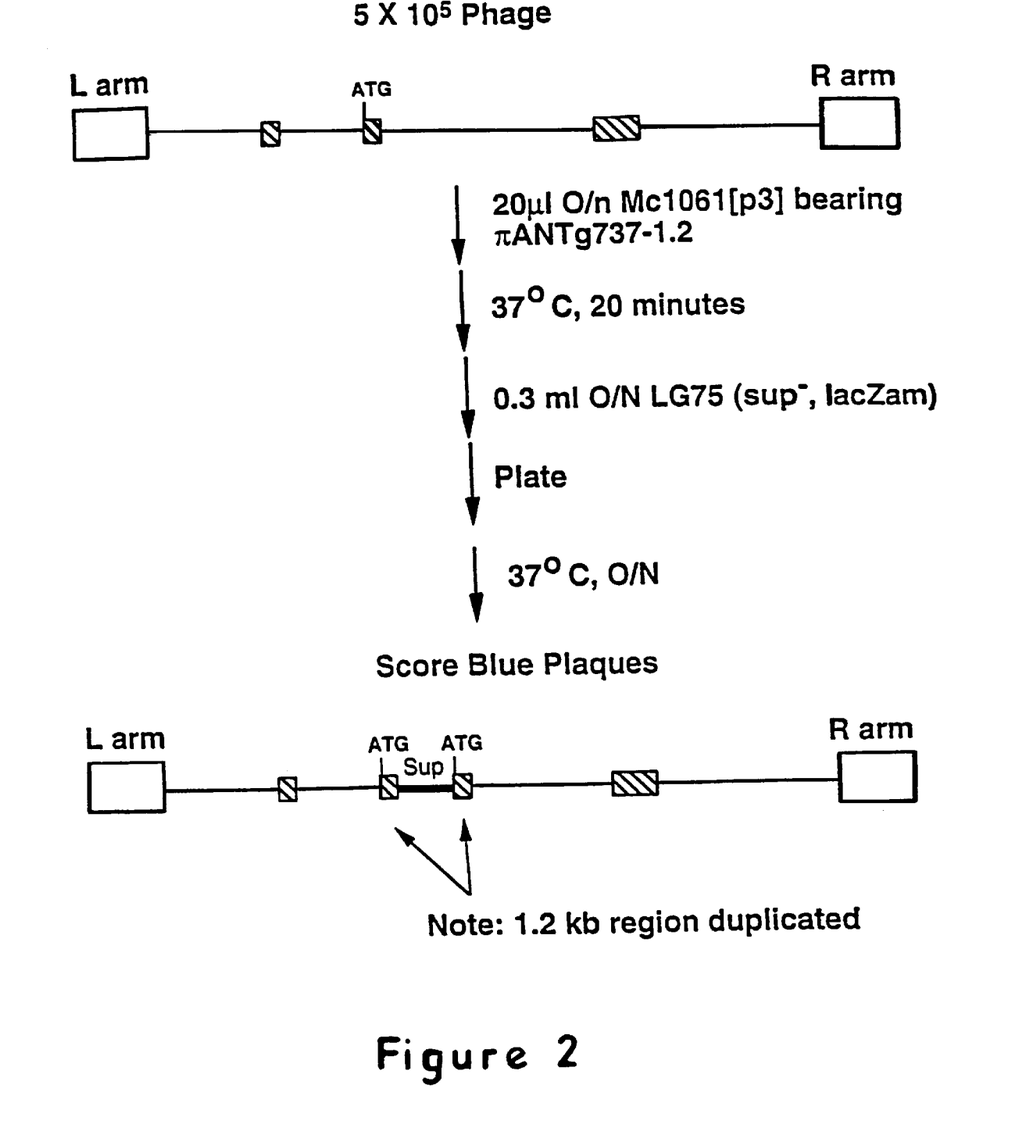
FIG. 2 depicts schematically, homologous recombination between πAN13 and a target phage containing homologous target sequences and a strategy for the single step selection for isolation of recombinant phage (targeting constructs).
Figure 3:
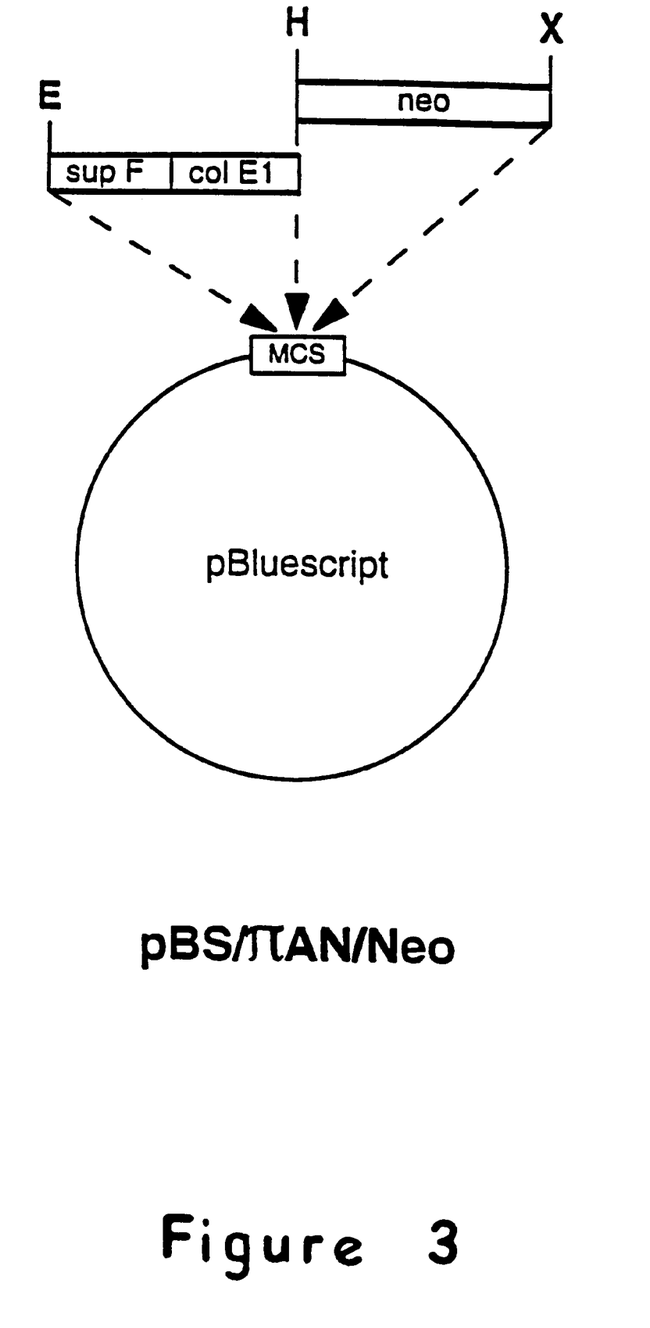
FIG. 3 shows the plasmid pBS/πAN/Neo used for double homologous recombination.

As depicted in FIG. 2, homologous recombination between the target phage [Syrinx 2A(Tg737-17)] and the probe plasmid (πANTg737-1.2) results in the integration of the supF gene into Tg737 gene segment of the target phage via its homologous Tg737 sequences and in the duplication of the probe DNA. The integration of supF gene into the recombinant phage was established by the production of active β-galactosidase in LG75 cells (sup0, LacZAM).

Integration of the probe DNA into homologous DNA in the target phage occurs by what is referred to as single homologous recombination and, as described above, results in the duplication of the probe plasmid sequences at the recombination site in the target phage. When the targeting construct having the duplication is introduced into the target genomic site in mammalian cells, the presence of such duplicated sequence may allow alternative splicing to occur after transcription of the disrupted gene thereby splicing out the disruption. However, the possibility of such alternative splicing may be minimized by preparing probe plasmids having a genomic or cDNA fragment of at least 20–40 bp that occur within the open reading frame of a single exon. This will cause a duplication of a part of the exon. The reading frame will shift and cause a disruption in gene expression if the size of the duplicated region is chosen carefully (i.e., not a multiple of 3 bp).

A simple one-step genetic selection was developed for detection of phage which have undergone homologous recombination with probe plasmid and is illustrated schematically in FIG. 2. Two criteria were used to establish that true homologous recombination had occurred.

First, integration of supF gene carried by the probe plasmid into target phage carried by the target phage generates recombinant phage which can grow in suppressor-less (or Sup°) host cells and by suppressing the amber mutation in genes for lytic growth and in the β-galactosidase of the phage thereby allowing the production of active β-galactosidase. These phage are easily detected by their ability to give rise to blue plaques when plated on suppressor-less, LacZAM cells such as *E. coli* LG75.

Second, homologous recombination is a reversible process. The frequency of reversal of homologous recombination event has been estimated to be on the order of $10^2$ to $10^3$ per generation. The frequency of excision of plasmid sequences was detected by propagation of recombinant phage in recombination-proficient host cells. The phages that have lost the SupF gene can only grow in supF+ (*E. coli* L392) host cells but not in SupF− host ceus (LG75).

Finally, homologous recombination was finally confirmed by restriction mapping using EcoRI, BamHI, SalI, Hindfi, XbaI or SacI. Based on this analysis and the known restriction map of πAN13 were shown to arise from homologous recombination between the target phage Syrinx 2A (Tg737-17) and the probe plasmid πAN13 (Tg737-1.2).

These studies establish that targeting constructs can be efficiently generated by single homologous recombination in bacteria according to the methods of the present invention, without the extensive DNA sequence information and without the detailed restriction mapping normally required by standard methods.

EXAMPLE 2

Double Homologous Recombination in Bacteria

As discussed above, targeting constructs generated by single homologous recombination have a duplication of sequences (portion of genomic or cDNA corresponding to region to be disrupted) at the insertion site in the target phage. However, it is possible to generate probe plasmids which are used for generating targeting constructs by double homologous recombination which do not result in duplicated target sequences.

Figure 4:
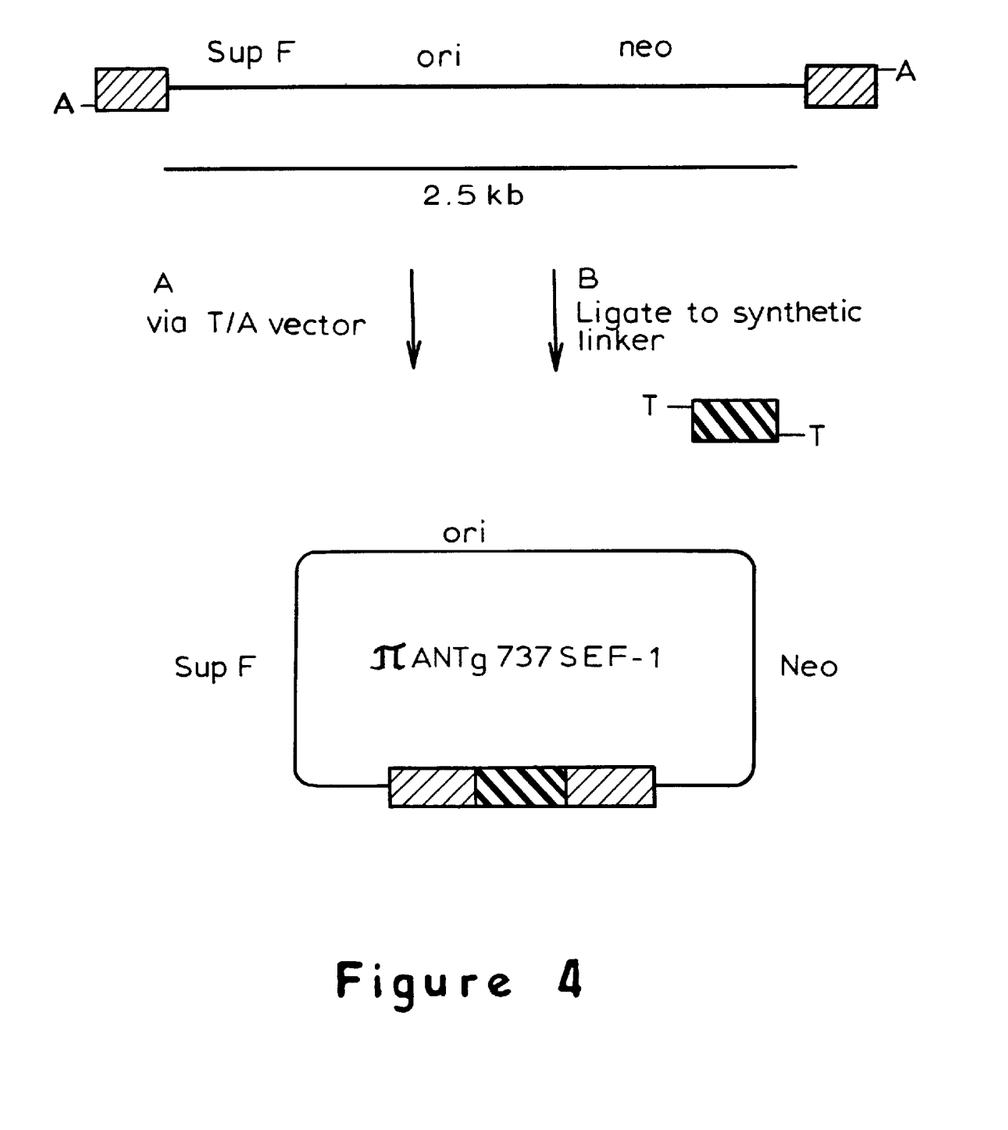
FIG. 4 shows the SEF πANTg737 SEF-1.

By way of example, a plasmid, pBS/πAN/neo, which contains the SupF gene and neo' gene is constructed as outlined in FIG. 4 by inserting a SupF gene, a colE1 gene and a neo' gene into the multiple cloning site of the plasmid pBluescript (Stratagene, La Jolla, Calif.). This plasmid is used as template to produce a plasmid/specific engineered fragment using chimeric primers in a PCR reaction. The chimeric primers preferably contain more than 40 bases of sequence corresponding to the 5' and 3' ends of exon II of the Tg737 gene and preferably 20 bases of sequences corresponding to the 5' of the SupF gene and the 3' end of the functional neo' gene of pBS/πAN/neo. Exemplary primers include,

CAAATGATGGAAAATGTTCATCTGGCAC-CAGAAACAGATG (SEQ ID NO: 1)

CTCAGTATCATAGGCTGGGTTG-TAGTCGTTGAAACCAGAG (SEQ ID NO: 2)

Circularization of the 2.5 kb PCR generated fragment is achieved by cloning in a T/A vector or by ligation with synthetic linker and thereby generating a plasmid, πTg737SEF1 (Tg737SEF1).

Figure 5:
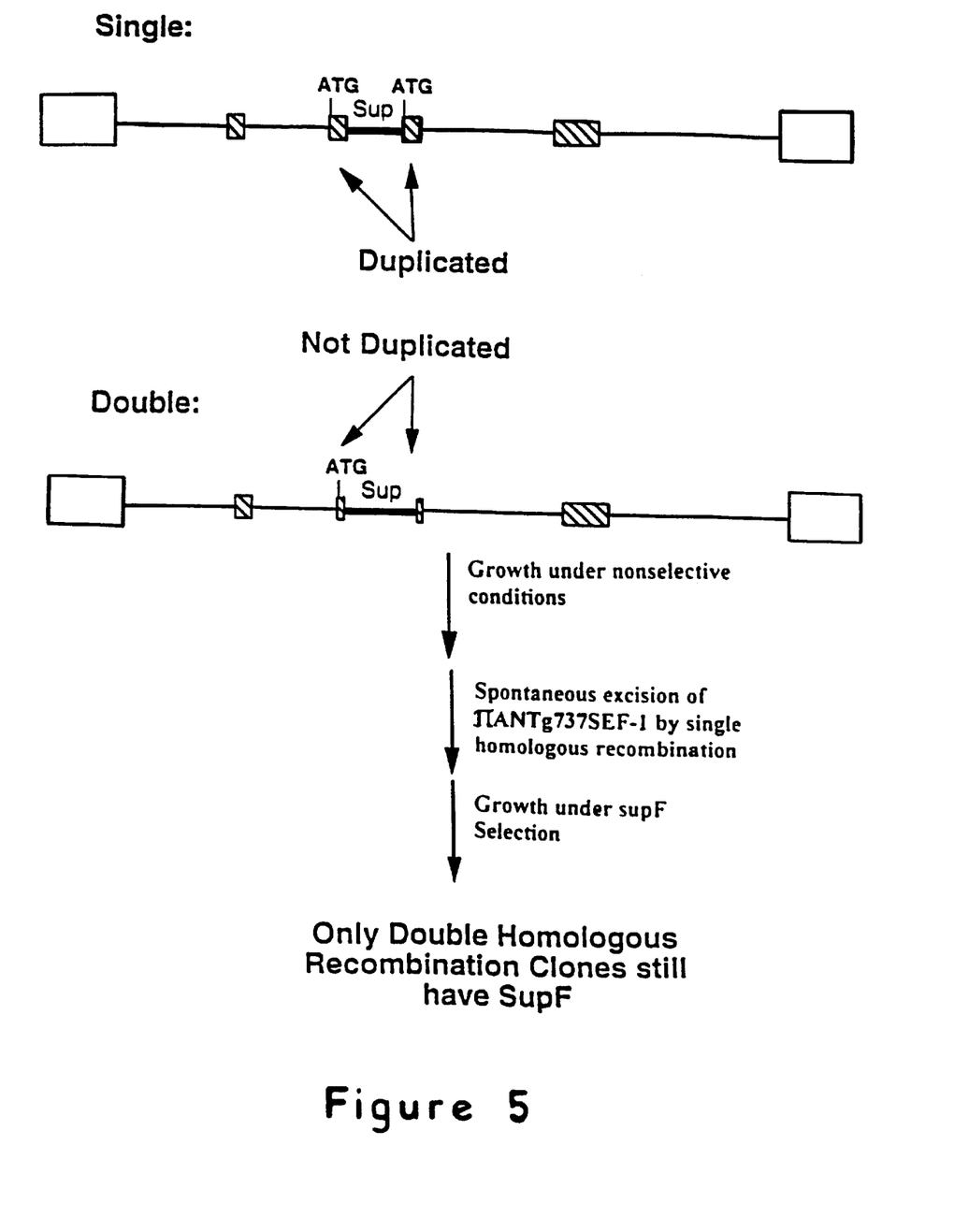
FIG. 5 depicts recombination products resulting from single homologous recombination and double homologous recombination.

The plasmid Tg737 SEF1 is then introduced into *E. coli* strain [Mc1061cp3] and the bacterial cells containing Tg737SEF1 are then infected with Syrinx 2A (Tg737-17) to recombine with the phage as described in Example 1. Recombinant phage are then selected according to the method set out in Example 1. The phage selected with this procedure can result from both single and double homologous recombination. Selection of recombinant phage resulting from double homologous recombination is accomplished by a scheme outlined in FIG. 5. Briefly, as illustrated in FIG. 5, recombinant phage may be grown under non-selective conditions. Phage having undergone a single homologous recombination event and the resulting duplication of probe sequences will undergo a spontaneous excision of the duplicated sequences which also results in the loss of the SupF gene. Phage are then plated on suppressor-less host cells wherein only the phage having undergone the double homologous recombination event will retain the SupF gene and its flanking probe DNA and will grow on the suppressorless cells.

Figure 6:
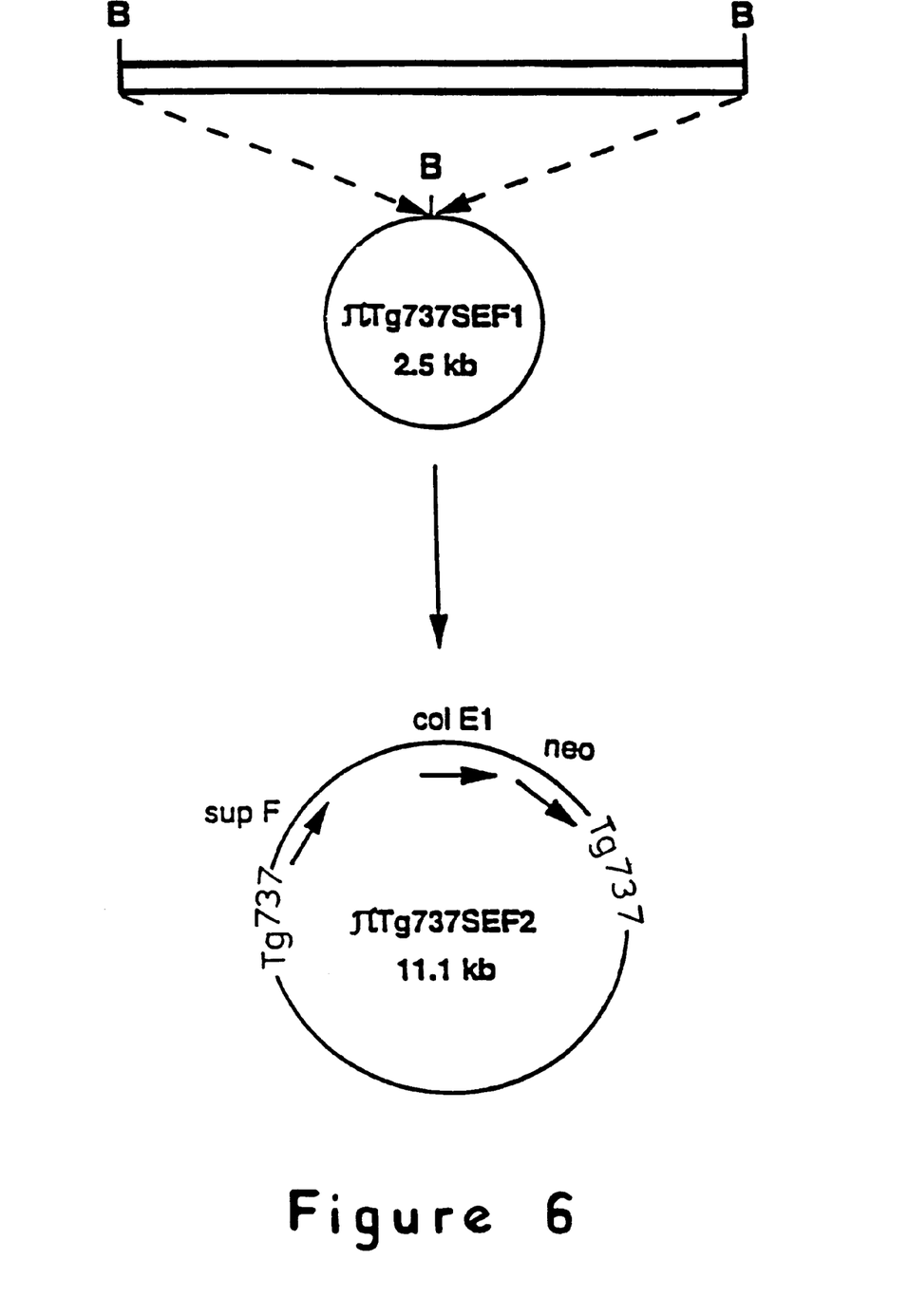
FIG. 6 shows the SEF πTg737 SEF-2.

For selection of double homologous recombination, a large plasmid, πTg737SEF2, derived from πTg737SEF1 is constructed by inserting the 8.6 kb BamHI fragment of the "stuffer" region of Syrinx 2A into the unique BamHI site of πTg737SEF1 (FIG. 6). The integration of the πTg737SEF2 plasmid into the target phage can occur by either single homologous recombination, in which case the entire plasmid will integrate, or by double homologous recombination, where only the SupF-neo cassette will integrate into the target via the homologous. The single homologous recombination event will be selected against because the integrated plasmid will make a phage genome too large to package into a single phage head. Therefore only the double homologous recombination event will be selected for.

As discussed in detail above, the foregoing examples demonstrate that targeting constructs may be produced efficiently, according to the present invention. Without detailed DNA sequence information or restriction mapping, thereby eliminating a critical bottle-neck in the generation of targeted mutations in amber. The foregoing examples are presented by way of illustration and are not intended to limit the scope of the invention as set out in the claims.

---

What is claimed is:

1. A method for producing gene targeting constructs in bacteria by single homologous recombination, the method comprising the steps of:
   a) preparing a probe plasmid comprising a marker cassette, the marker cassette comprising a suppressor t-RNA gene and a mammalian cell selectable marker, wherein the marker cassette is flanked on at least one side by probe DNA, wherein the probe DNA comprises at least a portion of an exon of a gene to be targeted;
   b) introducing the probe plasmid of step a) into a population of homologous recombination proficient suppressor-free bacterial host cells;
   c) preparing a target phage, the target phage comprising at least one suppressible mutation in a gene necessary for phage growth and a target DNA comprising a portion of a genomic region to be targeted and wherein the target DNA is homologous to all or part of the probe DNA of step a);
   d) infecting the population of bacterial cells of step b) with the phage of step c), allowing recombination between the probe DNA and the target DNA;
   e) allowing homologous recombination between the probe plasmid and the target phage; and
   f) isolating phage produced in step d).

2. The method of claim 1 step a) wherein the probe sequence comprises from about 15 to 20 kb of genomic DNA.

3. The method of claim 1 wherein the probe DNA flanking the marker cassette comprises from at least about 20 bp to about 40 bp.

4. The method of claim 1 wherein the target DNA comprises from about 15 kb to about 20 kb.

5. The method of claim 1 wherein the suppressor tRNA gene is SupF.

6. The method of claim 1 wherein the mammalian cell selectable marker is a neo gene.

7. The method of claim 6 wherein the neo gene is operatively linked to a promoter which allows expression of the neo gene in embryonic stem cells.

8. The method of claim 1 wherein the phage is a lambda phage.

9. The method of claim 1 wherein the suppressible mutation in the phage is an amber mutation.

10. A targeting construct obtainable by the method of claim 1.

11. A targeting construct produced by the methods of claim 1.

12. A method for obtaining a targeting construct, the method comprising culturing under suitable nutrient and environmental conditions, a population of homologous recombination proficient bacterial cells comprising target phage and a probe plasmid and isolating therefrom, phage resulting from homologous recombination between the target phage and probe plasmid.

13. The method of claim 12 wherein the probe plasmid is a plasmid/SEF.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:

```
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:1:

CAAATGATGG AAAATGTTCA TCTGGCACCA GAAACAGATG                            40

(2) INFORMATION FOR SEQ ID NO:2:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:2:

CTCAGTATCA TAGGCTGGGT TGTAGTCGTT GAAACCAGAG                            40
```